United States Patent [19]

Fujino et al.

[11] Patent Number: 4,487,726

[45] Date of Patent: Dec. 11, 1984

[54] 4-METHOXY-2,3,6-TRIMETHYLBEN-ZENESULFONYL CHLORIDE

[75] Inventors: Masahiko Fujino, Takarazuka; Osamu Nishimura, Toyonaka, both of Japan

[73] Assignee: Takeda Chemical Industries, Ltd., Osaka, Japan

[21] Appl. No.: 420,710

[22] Filed: Sep. 21, 1982

Related U.S. Application Data

[62] Division of Ser. No. 233,641, Feb. 11, 1981, Pat. No. 4,368,150.

Foreign Application Priority Data

Feb. 12, 1980 [JP] Japan .................. 55-16456
Nov. 4, 1980 [JP] Japan .................. 55-154919
Jan. 5, 1981 [JP] Japan .................. 56-560

[51] Int. Cl.$^3$ .................................. C07C 143/70
[52] U.S. Cl. .................................. 260/543 R
[58] Field of Search .................. 260/543 R, 543 F

[56] References Cited

U.S. PATENT DOCUMENTS 3,453,099 7/1969 Popoff et al. .................. 260/543 F

OTHER PUBLICATIONS

Baliah, V. et al., *J. Indian Chem. Soc.*, vol. 40, (1963), pp. 381-383.
Fujino, Masahiko et al., *J.C.S. Chem. Comm.*, Aug. 19, 1980, pp. 668-669.

*Primary Examiner*—Natalie Trousof
*Assistant Examiner*—L. Hendriksen
*Attorney, Agent, or Firm*—Wenderoth, Lind & Ponack

[57] ABSTRACT

A guanidino group in an amino acid or a peptide can be protected with a specific group, i.e. pentamethylbenzenesulfonyl, 2,4,6-trimethoxybenzenesulfonyl, 4-methoxy-2,3,5,6-tetramethylbenzenesulfonyl, 4-methoxy-2,6-dimethylbenzenesulfonyl or 4-methoxy-2,3,6-trimethylbenzenesulfonyl, and said group may easily be removed without affecting the amino acid or the peptide to be derived from the protected amino acid or peptide. Thus, the present invention is useful in the synthesis of peptides containing the guanidino group.

1 Claim, No Drawings

4-METHOXY-2,3,6-TRIMETHYLBENZENESULFONYL CHLORIDE

This application is a division of application Ser. No. 233,641, filed Feb. 11, 1981, now U.S. Pat. No. 4,368,150.

This invention relates in one aspect, to a method of producing peptides involving the protection of a guanidino group and, in another aspect, to an arginine derivative or a salt thereof useful for the production of peptides.

For the production of a peptide using a starting compound containing a guanidino

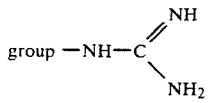

(e.g. arginine), the guanidino group must be protected beforehand. Protection of a guanidino group has heretofore been carried out by means of a nitro group or a tosyl group.

In such conventional processes, the elimination of the protective group has been possible only with poor yields. To remove the tosyl group, the elimination reaction must be conducted using anhydrous hydrogen fluoride under severe conditions, which tend to decompose the other moieties of the peptide to give by-products and detract from the yield of the peptide.

To overcome this disadvantage, the present inventors developed and practiced a synthetic method involving the use of certain guanidino-protecting groups, such as p-methoxybenzenesulfonyl and mesitylenesulfonyl, which are easily removable with methanesulfonic acid (Japanese Patent Application Laid open No. 100030/1976). The subsequent studies by the present inventors on the protection of guanidino led to the discovery that 4-methoxy-2,6-dimethylbenzenesulfonyl, pentamethylbenzenesulfonyl, 2,4,6-trimethoxybenzenesulfonyl, 4-methoxy-2,3,5,6-tetramethylbenzenesulfonyl and 4-methoxy-2,3,6-trimethylbenezenesulfonyl can be easily eliminated from the corresponding protected amino acids or peptide under mild acidic conditions.

Thus, an object of this invention is to provide a method for producing a guanidino-containing peptide which comprises protecting the guanidino group of a guanidino-containing starting material with a substituted benzenesulfonyl group of the following general formula (I):

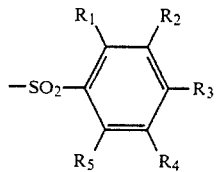

wherein $R_1$, $R_3$ and $R_5$ are methyl or methoxy, and $R_2$ and $R_4$ are hydrogen or methyl, provided that when $R_3$ is methyl, all of $R_1$, $R_2$, $R_4$ and $R_5$ are methyl; when $R_3$ is methoxy, and $R_2$ and $R_4$ are both hydrogen, $R_1$ and $R_5$ are both methoxy; or when $R_3$ is methoxy and, at the same time, $R_1$ and $R_5$ are both methyl, $R_2$ is hydrogen or methyl and $R_4$ is hydrogen or methyl, respectively, subjecting the protected compound to a peptide synthesis reaction and removing the protective group with an acid.

Another object of this invention is to provide an arginine derivative, inclusive of a salt thereof, which has the general formula (II):

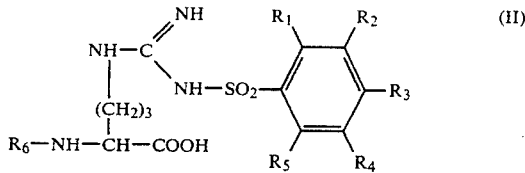

wherein $R_1$ to $R_5$ are of the same meaning as defined in Formula (I) and $R_6$ is hydrogen or an α-amino-protecting group.

A further object of this invention is to provide 4-methoxy-2,3,6-trimethylbenzenesulfonyl halide.

In introducing a substituted benzenesulfonyl group of formula (I) into the guanidino group of said guanidino-containing starting compound, the α-amino group of the guanidino-containing compound is previously protected. Protection of the α-amino group can be accomplished by means of a conventional protective group. For example, as the protective group $R_6$ in general formula (II), there may be mentioned carbobenzoxy, p-nitrobenzyloxycarbonyl, p-methoxybenzyloxycarbonyl, t-butoxycarbonyl, t-amyloxycarbonyl, 9-fluorenylmethoxycarbonyl, isonicotinyloxycarbonyl, o-nitrophenylsulfenyl, 2-(p-biphenyl)isopropyloxycarbonyl, etc., respectively as introduced in the per se known manner. Particularly advantageous are the compounds protected with carbobenzoxy or t-butoxycarbonyl.

Then, the guanidino group of the guanidino-containing compound with its α-amino group thus protected is reacted with a substituted benzenesulfonyl group of general formula (I). This reaction is accomplished by reacting about 1 to 5 equivalents, preferably about 1 to 2 equivalents, of the substituted benzenesulfonyl compound (I) with the guanidino-containing compound. The sulfonyl group is usually employed as a halide.

The halide may be any of the chloride, fluoride, bromide and iodide. In this invention, 4-methoxy-2,3,6-trimethylbenzenesulfonyl chloride, one of the substituted benzenesulfonyl groups (I), can be produced as a crystal, without the formation of isomer, by reacting 2,3,5-trimethylanisole with chlorosulfonic acid.

Introduction of a substituted benzenesulfonyl group of formula (I) is preferably carried out in the presence of a base. The base may for example be sodium hydroxide, potassium hydroxide or lithium hydroxide and is employed in a proportion of about 1 to 10 equivalents, preferably about 1 to 5 equivalents, to each mole of guanidino-containing compound. Usually, this reaction is desirably conducted in a suitable solvent such as water, acetone, dioxane, dimethyl-formamide or tetrahydrofuran or a mixture of such solvents. This reaction is carried out at $-10°$ C. to $+25°$ C. and preferably at $-5°$ C. to $+10°$ C.

The resulting guanidino-containing compound with its guanidino group protected with a substituted benzenesulfonyl group of formula (I) is subjected, as it is in the free form or after being converted to the cyclohexylamine, dicyclohexylamine, sodium or other salt in the per se conventional manner, to the desired peptide condensation reaction.

In the context of this invention, the guanidino-containing compound with its guanidino group protected with a substituted benzenesulfonyl group (I) is any of the arginine derivatives of general formula (II) and salts thereof.

The guanidino-containing compound with its guanidino group protected with a substituted benzenesulfonyl group of general formula (I) is subjected to a desired peptide condensation reaction in the conventional manner. As examples of such conventional manner, there may be mentioned those procedures mentioned in M. Bodansky and M. A. Ondetti Peptide Synthesis, Interscience, New York, 1966, F. M. Finn and K. Hormann: The Proteins, Vol. 2, H. Nenrath, R. L. Hill (ed.), Academic Press Inc., New York, 1976; Izumiya N. et al: Peptide Gosei (Peptide Synthesis), Maruzen (K.K.), 1975, etc., such as the azide process, chloride process, acid anhydride process, mixed acid anhydride process, DCC process, activated ester process, the process involving the use of Woodward's reagent K, carbodiimidazole process, redox process, DCC/HONB process and so on.

The peptide condensation reaction is now carried out. Then, the protective group according to this invention is eliminated by means of an acid. To remove this protective group, any of the conventional acid treatments can be employed, such as the methanesulfonic acid process, trifluoromethanesulfonic acid process, etc. Moreover, in the case of the method of this invention, the use of trifluoroacetic acid can be proposed as a new method of acid treatment. This elimination reaction proceeds very satisfactorily especially when it is conducted in the presence of thioanisole or anisole.

As regards the amounts of said trifluoroacetic acid and said thioanisole or anisole, it is advantageous to employ such amounts as are useful as solvents and are enough to remove the protective group. For example, they are used in a proportion of 1 to $10^5$ equivalents, preferably 1 to $10^3$ equivalents, per mole of the compound having the protected guanidino group. This deprotecting reaction may be carried out in a solvent such as acetic acid, chloroform or methylene chloride, and at a temperature from about $-10°$ C. to about $+300°$ C., preferably at about $+10°$ C. to about $+100°$ C.

The method according to this invention is applicable to the production of any guanidino-containing peptide. As typical examples of such peptides, there may be mentioned physiologically active peptides such as Des-Gly$^{10}$-[D-Leu$^6$]-LH-RH-ethylamide (Japanese Patent Publication No. 14072/1978), Des-Gly$^{10}$-LH-RH-ethylamide (Japanese Patent Publication No. 24423/1978), Tuftsin (Nature 228, 672, 1970), Substance P, Kyotorphin, etc. Other peptides, such as MSH, ACTH, Glucagon-Secretin, Bradykinin, Dynorphin and $\alpha$-Neoendorphin, as well as active fragments of such peptides, can also be produced advantageously.

The substituted benzenesulfonyl group of general formula (I) in accordance with this invention can be easily removed not only by the acid guanidino-deprotecting reactions heretofore known but by an acid treatment under still milder conditions. For example, although a mild acid treatment with trifluoroacetic acid cannot be applied to the removal of the hitherto-known guanidino-protecting groups, it can be successfully utilized in the elimination of the substituted benzenesulfonyl group of general formula (I).

In the conventional processes involving the protection of guanidino with p-methoxybenzenesulfonyl or mesitylenesulfonyl and a subsequent deprotection with methanesulfonic acid after a peptide condensation, a succinimide type side-reaction may take place if the peptide includes an asparagine or aspartic acid residue or an N O acyl rearrangement reaction may take place if a serine or thereonine residue is present. In accordance with this invention, even if the peptide contains these types of amino acid residues, the protective group can be removed with a mild acid such as trifluoroacetic acid without inducing the above-mentioned side reactions.

This invention will hereinafter be described in detail by way of working and test examples. In the present specifications, amino acids, peptides, protective groups, activated groups, etc. are sometimes designated by the abbreviations recommended by IUPAC-IUB Commision on Biological Nomeclature or these employed commonly in the field of art. The following is a partial list of such abbreviations.

pGlu: pyroglutamic acid
His: histidine
Trp: tryptophane
Ser: serine
Tyr: tyrosine
Leu: leucine
Gly: glycine
Arg: arginine
Pro: proline
Lys: lysine
Gln: glutamine
Phe: phenylalanine
Met: methionine
Thr: threonine
(The above amino acids are L-amino acids unless otherwise indicated. The D-acids will be specifically indicated. Gly is an exception).
Z: carbobenzoxy
Boc: t-butoxycarbonyl
HONB and ONB: N-hydroxy-5-norbornene-2,3-dicarboximide and its ester
HOBt: N-hydroxybenzotriazole
DCC: N,N'-dicyclohexylcarbodiimide
DCU: N,N-dicyclohexylurea
H$_2$/Pd: catalytic reduction
TFA: trifluoroacetic acid
CHA: cyclohexylamine
OTCP: 2,4,5-trichlorophenyl ester
OSu: N-hydroxysuccinimide ester
Et: ethyl Further, in the present specification, the substituted benzenesulfonyl groups of general formula (I) will sometimes be designated by the following abbreviations.

4-Methoxy-2,6-dimethylbenzenesulfonyl as MDS
4-Methoxy-2,3,6-trimethylbenzenesulfonyl as Mtr
Pentamethylbenzenesulfonyl as Pme
2,4,6-Trimethoxybenzenesulfonyl as Tms
4-Methoxy-2,3,5,6-tetramethylbenzenesulfonyl as Tmo

EXAMPLE 1

(1) Synthesis of Z-Arg(MDS)-OH-CHA salt

In a mixture of 150 ml of 4N-NaOH and 400 ml of acetone is dissolved 46.2 g (0.15M) of Z-Arg-OH at room temperature and the solution was cooled with ice. A solution of 70.7 g (0.30M) of 4-methoxy-2,6-dimethylbenzenesulfonyl chloride in 150 ml of acetone is added dropwise to this solution over an hour. The mixture was stirred at room temperature for 2 hours and solid citric acid was added to make the reaction solution acidic. The acetone was distilled off and the resulting oily substance was extracted with ethyl acetate. The ethyl acetate layer was washed twice with water and the contemplated compound was extracted with aqueous $NaHCO_3$. The water layer was made acidic with citric acid and the resulting oily substance was extracted with ethyl acetate. The ethyl acetate layer was thoroughly washed with water and dried, and the ethyl acetate was distilled off under reduced pressure to obtain 63 g of oil. This oil was dissolved in 300 ml of ethyl acetate, and when cold, 14.3 ml of cyclohexylamine (CHA) was added. The mixture was allowed to stand at room temperature overnight and the resulting crystals were collected by filtration and recrystallized from acetonitrile.

Yield, 48.0 g (52.8%); m.p. 140°–141° C.

Optical rotation $[\alpha]_D^{23} + 5.7°$ (c=0.5, methanol), Thin layer chromatography (TLC): $Rf_1$ ($CHCl_3$-methanol-acetic acid=9:1:0.5)=0.25

Elemental analysis: Calcd. for $C_{23}H_{30}O_7N_4S \cdot C_6H_{13}N$: C, 57.50; H, 7.15; N, 11.56; S, 5.29. Found: C, 57.23; H, 6.96; N, 11.66; S, 5.32.

(2) Synthesis of H-Arg(MDS)-OH

In 150 ml of methanol was dissolved 4.23 g (0.007M) of Z-Arg(MDS)-OH-CHA salt, and catalytic reduction was carried out in the conventional manner using palladium black as the catalyst. The catalyst was filtered off and the filtrate was concentrated under reduced pressure. To the residue was added water and the resulting crystals were collected by filtration and recrystallized from water.

Yield 2.15 g (80.5%); m.p. 120°–122° C. (decomp.).

Optical rotation $[\alpha]_D^{23} - 7.8°$ (c=0.7, methanol).

TLC: $Rf_2$ (ethyl acetate-pyridine-acetic acid-water=30:20:6:11)=0.16; $Rf_4$ (n-butanol-ethyl acetate-water=1:1:1:1)=0.52.

Elemental analysis: Calcd. for $C_{15}H_{24}O_5N_4S \cdot \frac{1}{2}H_2O$: C, 47.23; H, 6.61; N, 14.69; S, 8.41. Found: C, 47.68; H, 6.58; N, 14.69; S, 8.47.

(3) Synthesis of Boc-Arg(MDS)-OH

In 1.65 ml of water was dissolved 1.12 g (0.003M) of H-Arg(MDS)-OH, and 0.63 ml (0.0045M) of triethylamine was added when cold. To this solution was added, under intense stirring, a solution of 793 mg (0.0033M) of t-butyl S-4,6-dimethylpyridimidine-2-ylthiolcarbonate in 1.65 ml of dioxane. The mixture was stirred at room temperature for 12 hours, at the end of which time the dioxane was distilled off. The residue was diluted with water and the water layer was washed with ethyl acetate. The water layer was then made acidic with 6N-HCl when cold and the resulting oil was extracted with ethyl acetate. The ethyl acetate layer was washed twice with water and dried, and the ethyl acetate was distilled off under reduced pressure. The crystals formed as above are treated with petroleum benzin, recovered by filtration and recrystallized from ethyl acetate.

Yield 1.35 g (95.7%); m.p. 175°–176° C. (decomp.).

Optical rotation $[\alpha]_D^{26} + 3.5°$ (c=0.5, methanol).

TLC: $Rf_1 = 0.34$.

Elemental analysis: Calcd. for $C_{20}H_{32}O_7N_4S$: C, 50.83; H, 6.83; N, 11.86; S, 6.79. Found: C, 50.96; H, 7.07; N, 11.56; S, 6.63.

TEST EXAMPLE

100 μmols of H-Arg(DMS)-OH were treated in:

(1) a mixture of trifluoroacetic acid (2 ml) and thioanisole (0.1 ml) at 50° C. for 1 hour;

(2) a mixture of trifluoroacetic acid (2 ml) and thioanisole (0.1 ml) at room temperature (21° C.) for 5 hours;

(3) a mixture of trifluoroacetic acid (2 ml) and anisole (0.1 ml) at 50° C. for 1 hour;

(4) a mixture of trifluoroacetic acid (2 ml) at 50° C. for 1 hour.

In each instance, the trifluoroacetic acid was distilled off under reduced pressure and the residue was dissolved in water and washed with ether once. The mixture was weighed to take 100 ml and analyzed for amino acids. The yield of arginine was thus determined. The results are shown in Table 1.

TABLE 1

|  | Temperature (°C.) | Time (hrs.) | Yield of Arg (%) |
|---|---|---|---|
| TFA-thioanisole (95:5) | 50 | 1 | 93.2 |
| TFA-thioanisole (95:5) | 21 | 5 | 89.3 |
| TFA-anisole (95:5) | 50 | 1 | 79.4 |
| TFA | 50 | 1 | 78.0 |

TFA: trifluoroacetic acid; amino acid analyzer: Hitachi Model 835

EXAMPLE 2

Synthesis of Z-Arg(MDS)-Pro-NHEt

In 70 ml of methanol was dissolved 2.76 g (0.01M) of Z-Pro-NHEt followed by addition of 1.90 g (0.01M) of p-toluenesulfonic acid. Then, catalytic reduction was carried out in the conventional manner using palladium black as the catalyst. The catalyst was filtered off and the filtrate was concentrated. The residue was dissolved in 50 ml of dimethylformamide, and under ice cooling, 1.40 ml (0.01M) of triethylamine was added. Then, Z-Arg(DMS)-OH [prepared from 6.06 g (0.01M) of Z-Arg(DMS)-OH-CHA salt] and hydroxybenzotriazole (1.54 g, 0.01M) were added and dissolved. To the solution was added 2.06 g (0.01M) of dicyclohexylcarbodiimide and the mixture was stirred for 24 hours. The resulting urea was filtered off and the filtrate was concentrated in vacuo. To the residue was added ethyl acetate and the ethyl acetate layer was washed with aqueous $NaHCO_3$ and 0.2N-HCl. The ethyl acetate was distilled off under reduced pressure. The residue was treated with petroleum benzin, and the resulting powdery solid was filtered off and purified by silica gel chromatography using chloroform as eluent.

Yield 3.5 g (56.6%); m.p. 65°–67° C.

Optical rotation $[\alpha]_D^{23} - 13.8°$ (c=0.5, dimethylformamide).

TLC: $Rf_1 = 0.47$.

Elemental analysis: Calcd. for $C_{29}H_{42}O_7N_6S$: C, 56.29; H, 6.84; N, 13.58; S, 5.18. Found: C, 56.56; H, 6.81; N, 13.40; S, 4.93.

EXAMPLE 3

Synthesis of Z-Leu-Arg(MDS)-Pro-NHEt

In 70 ml of methanol was dissolved 3.16 g (0.0051M) of Z-Arg(MDS)-Pro-NHEt followed by addition of 969 mg (0.0051M) of p-toluenesulfonic acid. Then, catalytic reduction was carried out in the conventional manner using palladium black as the catalyst. The catalyst was filtered off and the filtrate was concentrated. The residue was dissolved in 30 ml of dimethylformamide, followed by addition of 0.71 ml (0.0051M) of triethylamine when cold and further addition of 2.40 g (0.0051M×1.1) of Z-Leu-ONB. The mixture was stirred for 12 hours. The solvent was distilled off in vacuo and the residue was dissolved in ethyl acetate. The ethyl acetate layer was washed with aqueous NaHCO$_3$ and 0.2N-HCl and, after drying, distilled off under reduced pressure. To the residue was added ether and the resulting precipitate was collected by filtration and reprecipitated from ethyl acetate-ether.

Yield 2.5 g (67.0%); m.p. 95°–100° C.

Optical rotation $[\alpha]_D^{23} - 22.0°$ (c=0.6, dimethylformamide).

TLC: $Rf_1 = 0.50$.

Elemental analysis: Calcd. for $C_{35}H_{53}O_8N_7S$: C, 57.44; H, 7.31; N, 13.40; S, 4.38. Found: C, 57.60; H, 7.29; N, 13.15; S, 4.28.

EXAMPLE 4

Synthesis of
pGlu-His-Trp-Ser-Tyr-(D)Leu-Leu-Arg(MDS)-Pro-NHEt

In 50 ml of methanol was dissolved 732 mg (0.001M) of Z-Leu-Arg(MDS)-Pro-NHEt, and catalytic reduction was carried out in the conventional manner using palladium black as the catalyst. The catalyst was filtered off and the filtrate was concentrated. The residue was dissolved in 10 ml of dimethylformamide. In this solution were dissolved 816 mg (0.001M) of pGlu-His-Trp-Ser-Tyr-(D)-Leu-OH and 717 mg (0.004M) of HONB. The solution was cooled to −10° C. with ice-NaCl and, after addition of 412 mg (0.002M) of dicyclohexylcarbodiimide, the mixture was stirred at −10° C. for 3 hours, at 0° C. for 10 hours and at room temperature for 24 hours. The by-product urea was filtered off and the filtrate was concentrated in vacuo. Ether was added to the residue and the resulting precipitate was collected by filtration and reprecipitated twice from acetonitrile.

Yield 1.15 g (81.6%); m.p. 105°–110° C. (decomp.).

Optical rotation $[\alpha]_D^{23} - 28.2°$ (c=0.6, dimethylformamide).

TLC: $Rf_2 = 0.20$.

Elemental analysis: Calcd. for $C_{68}H_{93}O_{15}N_{16}S \cdot H_2O$: C, 57.33; H, 6.72; N, 15.73; S, 2.25. Found: C, 57.29; H, 7.18; N, 15.32; S, 2.02.

EXAMPLE 5

Synthesis of
pGlu-His-Trp-Ser-Tyr-(D)-Leu-Leu-Arg-Pro-NHEt

In a mixture of 0.5 ml of thioanisole and 10 ml of trifluoroacetic acid was dissolved 300 mg of pGlu-His-Trp-Ser-Tyr-(D)-Leu-Leu-Arg(MDS)-Pro-NHEt and the solution was left standing at 50°–55° C. for 1 hour. The trifluoroacetic acid was distilled off under reduced pressure, ether was added to the residue and the resulting precipitate was collected by filtration. The precipitate was dissolved in a small amount of water and the solution was passed through a column (1.5×10 cm) of Amberlite IRA-410 (acetate-form). The effluent and washings were combined and directly passed onto a column (1.5×12 cm) of carboxymethyl-cellulose. The column was washed with 50 ml of water and elution was carried out by the linear gradient method using water (500 ml) and 0.15M ammonium acetate (500 ml, pH 6.9). The main fractions (240 to 390 ml) were cooled, lyophilized and dissolved in a small amount of 1N-acetic acid. The solution was passed through a column (2.5×120 cm) of Sephadex LH-20 and elution was carried out with the same solvent system as above. The main fractions (290–350 ml) were pooled and lyophilized.

Yield 120 mg.

Optical rotation $[\alpha]_D^{23} - 34.1°$ (c=0.4, 5% acetic acid).

TLC: $Rf_3$ (n-butanol-pyridine-acetic acid-water=30:20:6:24)=0.56

Amino acid analysis (acidolysis): His, 1.01(1); Arg+ethylamine, 1.75(1+1); Trp, 0.90(1); Ser, 0.86(1); Glu, 1.05(1); Pro, 1.04(1); Leu, 2.03(2); Tyr, 1.11(1); Average recovery 85.0%

EXAMPLE 6

Synthesis of
pGlu-His-Trp-Ser-Tyr-Gly-Leu-Arg(MDS)-Pro-NHEt

Employing 476 mg (0.00065M) of Z-Leu-Arg(MDS)-Pro-NHEt and 494 mg (0.00065M) of pGlu-His-Trp-Ser-Tyr-Gly-OH, the contemplated compound were prepared by a procedure similar to that described in Example 4.

Yield 710 mg (80.9%), m.p. 135°–140° C. (decomp.).

Optical rotation $[\alpha]_D^{23} - 26.7°$ (c=0.5, dimethylformamide);

$Rf_2 = 0.16$.

Elemental analysis: Calcd. for $C_{64}H_{85}O_{15}N_{16}S \cdot H_2O$: C, 56.16; H, 6.41; N, 16.38; S, 2.34. Found: C, 56.15; H, 6.71; N, 16.11; S, 2.18.

EXAMPLE 7

Synthesis of
pGlu-His-Trp-Ser-Tyr-Gly-Leu-Arg-Pro-NHEt

Employing 300 mg of Arg(MDS)-Pro-NHEt, the contemplated compound was synthesized by a proceduce similar to that in Example 5.

Yield 122 mg.

Optical rotation $[\alpha]_D^{23} - 55.2°$ (c=0.5, 5% acetic acid).

TLC: $Rf_4 = 0.48$ (Avicel).

Amino acid analysis (acidolysis): His, 1.02(1); Arg+ethylamine, 1.83(1+1); Trp, 1.01(1); Ser, 0.81(1); Glu, 1.04(1); Pro, 1.00(1); Leu, 1.03(1); Tyr, 1.03(1); Gly, 1.07(1), Average recovery, 90.0%.

EXAMPLE 8

Synthesis of Boc-Arg(MDS)-Pro-Lys(Boc)-Pro-OH

In 50 ml of methanol was dissolved 590 mg (0.001M) of oily Z-Pro-Lys(Boc)-Pro-Ome as synthesized by serial condensation reaction of H-Pro-OMe with Z-Lys(Boc)-ONB and Z-Pro-ONB, and catalytic reduction was carried out in the conventional manner using palladium black as the catalyst. The catalyst was filtered off and the filtrate was concentrated under reduced pressure. The residue was dissolved in 10 ml of dimethylformamide, followed by addition of 473 mg (0.001M) of Boc-Arg(MDS)-OH and 153 mg (0.001M) of hydroxybenzotriazole. The mixture was reacted at room temperature for 12 hours. The resulting urea was filtered off and the filtrate was concentrated in vacuo. The residue was dissolved in ethyl acetate and the ethyl acetate layer was washed with aqueous NaHCO$_3$ and 0.2N-HCl and, after drying, the ethyl acetate was distilled off under reduced pressure. The oily residue [Boc-Arg(MDS)-Pro-Lys(Boc)-Pro-OMe] was washed well with petroleum benzin and dissolved in 10 ml of methanol, followed by addition of 2 ml of 1N-NaOH when cold. The saponfication reaction was carried out at room temperature for 2 hours. Then, 2 ml of 1N-HCl was added dropwise when cold and the reaction mixture was diluted with water. The resulting oily substance was extracted with ethyl acetate. The ethyl acetate layer was washed with water and dried. The ethyl acetate was distilled off under reduced pressure and the residue was treated with petroleum benzin and recovered by filtration. The resulting powder was reprecipitated from ethyl acetate-ether.

Yield 530 mg (58.3%); m.p. 85°–90° C.

Optical rotation $[\alpha]_D^{26} -35.6°$ (c=0.5, dimethylformamide); TLC: $Rf_1=0.33$.

Elemental analysis: Calcd. for $C_{42}H_{68}O_{12}N_8S$: C, 54.94; H, 7.58; N, 12.21; S, 3.49. Found: C, 55.02; H, 7.65; N, 12.08; S, 3.63.

EXAMPLE 9

Synthesis of Boc-Arg(MDS)-Pro-Lys(Boc)-Pro-Gln-Gln-Phe-Phe-Gly-Leu-Met-NH$_2$ In a mixture of trifluoroacetic acid (4.5 ml) and water (0.5 ml) was dissolved 485 mg of Boc-Gln-Gln-Phe-Phe-Gly-Leu-Met-NH$_2$ [J. Bergmann, M. Bienert, H. Niedvich, B. Mehlis and P. Oehme, Experientia, 30, 401 (1974)] and the solution was shaken at 10° C. for 20 minutes. After 0.5 ml of 1N-HCl was added, the mixture was distilled under reduced pressure. Then, ether was added to the residue and the precipitate was collected by filtration and dried over sodium hydroxide. The resulting dry powder was dissolved in 15 ml of dimethylformamide followed by the addition of 0.07 ml (0.0005M) of triethylamine when cold. In the mixture was dissolved 448 mg (0.0005M) of Boc-Arg(MDS)-Pro-Lys(Boc)-Pro-OH and 179 mg (0.001M) of HONB. To the solution was added 155 mg (0.0075M) of dicyclohexylcarbodiimide and the mixture was stirred for 24 hours. The by-product urea was filtered off and the filtrate was concentrated. Water was added to the residue, and the resulting precipitate was collected by filtration and reprecipitated twice from ethanol.

Yield 500 mg (56.8%), m.p. 245°–247° C. (decomp.).

Optical rotation $[\alpha]_D^{26} -34.0°$ (c=0.5, dimethylformamide), TLC: $Rf_2=0.83$.

Elemental analysis: Calcd. for $C_{83}H_{126}O_{20}N_{18}S_2$: C, 56.64; H, 7.22; N, 14.32; S, 3.63. Found: C, 56.50; H, 7.15; N, 14.28; S, 3.73.

EXAMPLE 10

Synthesis of H-Arg-Pro-Lys-Pro-Gln-Gln-Phe-Phe-Gly-Leu-Met-NH$_2$ (Substance P)

In a mixture of 1 ml of thioanisole and 10 ml of trifluoroacetic acid is dissolved 100 mg of Boc-Arg(MDS)-Pro-Lys(Boc)-Pro-Gln-Gln-Phe-Phe-Gly-Leu-Met-NH$_2$ and the solution was shaken at 50° C. for 2 hours. The trifluoroacetic acid was distilled off under reduced pressure, ether was added to the residue, and the resulting precipitate was collected by filtration, dried over sodium hydroxide in vacuo, and dissolved in a small amount of water. To the solution was added 3 ml of Amberlite IRA-410 (acetate-form) and the mixture was shaken for a while. The resin was then filtered off and the filtrate was lyophilized. The powdery lyophilizate was dissolved in a small amount of 30% aqueous acetic acid. The solution was poured into a column (2.5×120 cm) of Sephadex G-25 and elution was carried out with the same solvent system as above. The main fractions (240–280 ml) were pooled and lyophilized.

Yield 67 mg.

Optional rotation $[\alpha]_D^{24} -80.7°$ (c=0.5, 5% acetic acid).

TLC: $Rf_3=0.53$ (Avicel).

Amino acid analysis (acidolysis): Lys, 0.99(1); Arg, 0.99(1); Glu, 2.03(2); Pro, 2.10(2); Gly, 0.99(1); Met, 0.99(1); Leu, 0.98(1); Phe, 1.96(2) Average recovery, 90.4%

EXAMPLE 11

Synthesis of Z-Pro-Arg(MDS)-OH

In 50 ml of dimethylformamide was dissolved 3.72 g (0.01M) of H-Arg(MDS)-OH, followed by addition of 1.40 ml (0.01M) of triethylamine when cold and further addition of 4.5 g (0.011M) of Z-Pro-ONB. The mixture was stirred at room temperature for 12 hours. To this reaction mixture was added 5 ml of acetic acid and the solvent was distilled off in vacuo. The residue was dissolved in ethyl acetate and the ethyl acetate layer was washed twice with water. The ethyl acetate was distilled off under reduced pressure and the residue was treated with petroleum benzin and filtered. The resulting powder was reprecipitated from ethyl acetate-petroleum benzin.

Yield 5.6 g (93.3%); m.p. 75°–80° C.

Optical rotation $[\alpha]_D^{23} -16.0°$ (c=0.6, dimethylformamide); TLC: $Rf_1=0.22$.

Elemental analysis: Calcd. for $C_{28}H_{37}O_8N_5S$: C, 55.71; H, 6.18; N, 11.60; S, 5.31. Found: C, 56.18; H, 6.58; N, 11.26; S, 4.73.

EXAMPLE 12

Synthesis of H-Pro-Arg(MDS)-OH

In 100 ml of methanol was dissolved 5.4 g (0.009M) of Z-Pro-Arg(MDS)-OH, and catalytic reduction was carried out in the conventional manner using palladium black as the catalyst. The catalyst was filtered off, the filtrate was concentrated, and the residue was dissolved in water and left standing in the cold. The resulting crystals were collected by filtration.

Yield 2.80 g(66.0%); m.p. 173°–174° C. (decomp.).

Optical rotation $[\alpha]_D^{23} -15.8°$ (c=0.6, dimethylformamide); TLC: $Rf_2=0.03$, $Rf_4=0.46$.

Elemental analysis: Calcd. for $C_{20}H_{32}O_6N_5S$: C, 51.05; H, 6.86; N, 14.88; S, 6.81. Found: C, 51.22; H, 6.95; N, 14.99; S, 6.86.

EXAMPLE 13

Synthesis of Z-Lys(Boc)-Pro-Arg(MDS)-OH

In 30 ml of dimethylformamide was dissolved 2.35 g (0.005M) of H-Pro-Arg(MDS)-OH, followed by addition of 0.7 ml of (0.005M) of triethylamine when cold and further addition of 2.80 g (0.005M) of Z-Lys(Boc)-OTCP. The mixture was stirred at room temperature for 12 hours. After 3 ml of acetic acid was added to the above mixture, the dimethylformamide was distilled off in vacuo. The residue was dissolved in ethyl acetate and the ethyl acetate layer was washed twice with water. The solvent was distilled off under reduced pressure and the residue was treated with ether. The resulting precipitate was collected by filtration and re-precipitated from ethyl acetate-ether.

Yield 3.30 g (79.3%); m.p. 85°–90° C.

Optical rotation $[\alpha]_D^{23} -19.3°$ (c=0.6, dimethylformamide); TLC: $Rf_1=0.25$.

Elemental analysis: Calcd. for $C_{39}H_{57}O_{11}N_7S \cdot \frac{1}{2}H_2O$: C, 55.70; H, 6.95; N, 11.66; S, 3.81. Found: C, 55.77; H, 7.03; N, 11.77; S, 3.65.

EXAMPLE 14

Synthesis of Boc-Thr-Lys(Boc)-Pro-Arg(MDS)-OH

In 100 ml of methanol was dissolved 3.00 g (0.0036M) of Z-Lys(Boc)-Pro-Arg(MDS)-OH, and catalytic reduction was carried out in the conventional manner using palladium black as the catalyst. The catalyst was filtered off and the filtrate was concentrated under reduced pressure. The residue was dissolved in 50 ml of dimethylformamide and after addition of 0.50 ml (0.0036M) of triethylamine when cold, Boc-Thr-ONB [prepared from 877 mg (0.004M) of Boc-Thr-OH] was added. The mixture was stirred at room temperature for 12 hours, 3 ml of acetic acid was then added and the solvent was distilled off in vacuo. The residue was dissolved in ethyl acetate and the ethyl acetate layer was washed twice with water. The ethyl acetate was distilled off under reduced pressure. The residue was treated with ether and the resulting powdery solid was collected by filtration and reprecipitated from ethyl acetate-ether.

Yield 2.3 g (71.0%); m.p. 85°–90° C.

Optical rotation $[\alpha]_D^{23} -20.2°$ (c=0.6, dimethylformamide); TLC: $Rf_1=0.14$.

Elemental analysis: Calcd. for $C_{40}H_{66}O_{13}N_8S$: C, 53.44; H, 7.40; N, 12.46; S, 3.57. Found: C, 53.30; H, 7.65; N, 12.47; S, 3.36.

EXAMPLE 15

Synthesis of H-Thr-Lys-Pro-Arg-OH (Tuftsin)

In a mixture of 0.5 ml of thioanisole and 10 ml of trifluoroacetic acid was dissolved 300 mg of Boc-Thr-Lys(Boc)-Pro-Arg(MDS)-OH, and the solution was allowed to stand at 50° C. for 1 hour. The trifluoroacetic acid was distilled off under reduced pressure. The residue was treated with ether, and the resulting precipitate was collected by filtration, dried and dissolved in a small amount of water. The solution was shaken with 10 ml of Amberlite IRA-410 (acetate-form) for 30 minutes. The resin was then filtered off and the filtrate was lyophilized. The powdery lyophilizate was dissolved in a small amount of water, and the solution was poured into a column (1.5×10 cm) of carboxymethyl-cellulose. Elution was carried out by the linear gradient method using water (300 ml) and 0.2M ammonium acetate (300 ml, pH 6.9). The main fractions (290 to 350 ml) were pooled and lyophilized. The resulting powder was dissolved in 1N acetic acid, and the solution was poured into a column (2.5×120 cm) of Sephadex LH-20 and elution was carried out with the same solvent system as above. The main fractions (270–310 ml) were pooled and lyophilized.

Yield 180 mg.

Optical rotation $[\alpha]_D^{23} -63.1°$ (c=0.6, 5% acetic acid).

TLC: $Rf_3=0.22$ (Avicel).

Amino acid analysis (acidolysis): Lys, 1.00(1); Arg, 1.02(1); Thr, 1.01(1); Pro, 0.97(1); Average recovery, 92.0%.

EXAMPLE 16

Synthesis of Boc-Tyr-Arg(MDS)-OH

In 30 ml of dimethylformamide was dissolved 1.91 g (0.005M) of H-Arg(MDS)-OH, followed by addition of 0.7 ml (0.005M) of triethylamine when cold and further addition of 1.89 g (0.005M) of Boc-Tyr-OSu. The mixture was stirred at room temperature for 12 hours. Then 5 ml of acetic acid was added and the dimethylformamide distilled off in vacuo. The residue was dissolved in ethyl acetate and the ethyl acetate layer was washed twice with water. The ethyl acetate was distilled off under reduced pressure. The residue was treated with ether and the resulting precipitate was collected by filtration and reprecipitated from ethyl acetate-ether.

Yield 2.70 g (84.9%); m.p. 85°–90° C.

Optical rotation $[\alpha]_D^{23} +0.6°$ (c=0.5, dimethylformamide); TLC: $Rf_1=0.14$.

Elemental analysis: Calcd. for $C_{29}H_{41}O_9N_5S$: C, 54.79; H, 6.50; N, 11.02; S, 5.04. Found: C, 54.94; H, 7.01; N, 10.66; S, 4.54.

EXAMPLE 17

Synthesis of H-Tyr-Arg-OH (Kyotorphin)

In a mixture of 0.5 ml of thioanisole and 10 ml of trifluoroacetic acid was dissolved 300 mg of Boc-Tyr-Arg(MDS)-OH, and the solution was left standing at 50°–55° C. for 1 hour. The trifluoroacetic acid was distilled off under reduced pressure. The residue was treated with ether, and the resulting precipitate was collected by filtration and dissolved in a small amount of water. The solution was shaken with 10 ml of Amberlite IRA-410 (acetic-form) for 30 minutes. The resin was filtered off and the filtrate was lyophilized. The powdery lyophilizate was dissolved in a small amount of water and poured into a column (1.5×10 cm) of carboxymethylcellulose. Elution was carried out by the linear gradient method using water (300 ml) and 0.1M ammonium acetate (300 ml, pH 6.9). The main fractions (100 to 150 ml) were pooled and lyophilized. The powdery lyophilizate was dissolved in a small amount of 1N-acetic acid. The solution was poured into a column (2.5×120 cm) of Sephadex LH-20 and elution was carried out with the same solvent system as above. The main fractions were pooled and lyophilized.

Yield 150 mg.

Optical rotation $[\alpha]_D^{21} -17.6°$ (c=0.4, water).

TLC: $Rf_3=0.45$ (Avicel).

Amino acid analysis (acidolysis): Arg, 1.06(1); Tyr, 0.94(1); Average recovery, 90.6%.

REFERENCE EXAMPLE 1

Synthesis of pentamethylbenzenesulfonyl chloride

In 500 ml of dichloromethane was dissolved 17.8 g of pentamethylbenzene and the solution was cooled to $-5° \sim -10°$ C. A solution of 24 ml of chlorosulfonic acid in 400 ml of dichloromethane was added dropwise, and the mixture was allowed to stand at room temperature. The reaction mixture was poured into ice-5% aqueous sodium hydrogen carbonate. The organic layer was washed with water and dried over magnesium sulfate. Removal of the solvent by distillation leaves crystals which were collected by filtration and recrystallized from n-hexane. Yield 27.7 g (93.5%), m.p. 80°–81° C.

Elemental analysis for $C_{11}H_{15}O_2SCl$: Calcd.: C, 53.54; H, 6.13; S, 13.00; Cl, 14.37. Found: C, 53.78; H, 6.09; S, 13.00; Cl, 14.39.

REFERENCE EXAMPLE 2

Synthesis of 2,4,6-trimethoxybenzenesulfonyl chloride

In 500 ml of dichloromethane is dissolved 5.05 g of 1,3,5-trimethoxybenzene and the solution was cooled to $-5° \sim -10°$ C. A solution of 6 ml of chlorosulfonic acid in 400 ml of dichloromethane was added dropwise, and the mixture was allowed to stand at room temperature. The reaction mixture was then treated as in Reference Example 1. The resulting product was crystallized from carbon tetrachloride and filtered. Yield 610 mg (6.3%), m.p. 126°–129° C.

Elemental analysis for $C_9H_{11}O_5SCl$: Calc.: C, 40.53; H, 4.16; S, 12.02; Cl, 13.30. Found: C, 40.79; H, 4.16; S, 11.84; Cl, 13.28.

EXAMPLE 18

(1) Synthesis of Z-Arg(Pme)-OH.CHA

In a mixed solution of 33 ml of 4N-NaOH and 130 ml of acetone was dissolved 10.0 g of Z-Arg-OH, and the mixture is ice-cooled. A solution of 14.0 g of pentamethylbenzenesulfonyl chloride in acetone (30 ml) was added dropwise and the mixture was stirred for 2 hours. The reaction mixture was acidified with citric acid, the solvent was distilled off and the residue was extracted with ethyl acetate. The ethyl acetate layer was extracted with aqueous $NaHCO_3$ and the extract was acidified with citric acid and extracted with ethyl acetate again, followed by drying over anhydrous sodium sulfate. After the solvent was distilled off, 3.55 ml of cyclohexylamine was added to the residue and the resultant salt was crystallized from ethyl acetate and collected by filtration.

Yield 13.3 g (66.4%), m.p. 173°–175° C., $[\alpha]_D^{23} +5.8°$ (c=1.27, methanol).

Elemental analysis for $C_{31}H_{47}O_6N_5S$: Calc.: C, 60.26; H, 7.67; N, 11.34; S, 5.19. Found: C, 60.15; H, 7.84; N, 11.25; S, 5.30.

(2) Synthesis of H-Arg(Pme)-OH

To 1.24 g of Z-Arg(Pme)OH-CHA was added 3 ml of $1N-H_2SO_4$, and the mixture was extracted with ethyl acetate. The solvent was distilled off and the residue was dissolved in 30 ml of methanol. Catalytic reduction was carried out in the presence of Pd black as catalyst. The catalyst was filtered off, the solvent distilled off, and the residue crystallized by addition of ether and filtered.

Yield 0.77 g (97.8%), m.p. 153°–156° C., $[\alpha]_D^{23} -5.5°$ (c=0.91, methanol).

Elemental analysis for $C_{17}H_{28}O_4N_4S.\frac{1}{2}H_2O$: Calcd.: C, 51.89; H, 7.43; N, 14.24; S, 8.15. Found: C, 51.60; H, 7.74; N, 13.80; S, 8.12.

EXAMPLE 19

(1) Synthesis of Z-Arg(Tms)-OH

In a mixed solution of 2.5 ml of 4N-NaOH and 10 ml of acetone is dissolved 0.77 g of Z-Arg-OH and the solution was ice-cooled. A solution (3 ml) of 1.0 g of 2,4,6-trimethoxybenzenesulfonyl chloride in acetone was added dropwise and the mixture was stirred for 2 hours. The reaction mixture was made acidic with citric acid, the solvent distilled off, and the residue saturated with NaCl and extracted with ethyl acetate. The extract was dried over anhydrous sodium sulfate and the solvent was distilled off. To the residue was added ether and the resulting powder was collected by filtration. The powder was dissolved in 10 ml of chloroform, subjected to silica gel column (4×10 cm) chromatography, elution being carried out with chloroform-methanol-acetic acid (9:0.7:0.35). The fractions from 110 ml to 210 ml were pooled, concentrated and precipitated from ether and the resulting powder was recovered by filtration.

Yield 250 mg (18.0%), m.p. 89°–93° C., $[\alpha]_D^{23} +0.8°$ (c=0.50, methanol).

Elemental analysis for $C_{23}H_{30}O_9N_4S.H_2O$: Calcd.: C, 49.63; H, 5.80; N, 10.07; S, 5.76. Found: C, 49.67; H, 5.57; N, 9.87; S, 5.81.

(2) Synthesis of H-Arg(Tms)-OH

Z-Arg(Tms)-OH (150 mg) was catalytically reduced in methanol using Pd black as catalyst. The catalyst was filtered off and the solvent was distilled off. To the residue was added ether and the resulting powder was collected by filtration.

Yield 105 mg (89.1%), m.p. 115°–120° C., $[\alpha]_D^{23} -8.9°$ (c=0.60, methanol).

Elemental analysis for $C_{15}H_{24}O_7N_4S.CH_3OH$: Calcd.: C, 44.02; H, 6.47; N, 12.84; S, 7.35. Found: C, 43.55; H, 6.33; N, 12.84; S, 6.99.

EXAMPLE 20

(1) Synthesis of 2,3,5,6-tetramethylanisole

In 150 ml of DMSO were dissolved 15.0 g of 2,3,5,6-tetramethylphenol and 28 ml of methyl iodide. Under ice-cooling 6.3 g of 60% sodium hydride in oil was added, and the mixture was stirred at room temperature for 1 hour. The excess sodium hydride was decomposed with MeOH and after addition of water extraction with ether was carried out. The extract was dried over sodium sulfate. Removal of the solvent by distillation leaves crystals which were recrystallized from MeOH.

Yield 10.2 g (62.1%), m.p. 45°–47° C.

(2) 4-Methoxy-2,3,5,6-tetramethylbenzenesulfonyl chloride

In 600 ml of dichloromethane was dissolved 10.0 g of 2,3,5,6-tetramethylanisole, followed by addition of a solution (400 ml) of 12 ml of chlorosulfonic acid in dichloromethane at $-5° \sim -10°$ C. The mixture was kept stirred for 2 hours and the reaction mixture was poured into ice-5% aqueous $NaHCO_3$. The organic layer was washed with water and dried over magnesium sulfate. The solvent was distilled off and the residue was crystallized from n-hexane and filtered.

Yield 10.0 g (62.5%), m.p. 58°–59° C.

Elemental analysis for $C_{11}H_{15}O_3SCl$: Calcd.: C, 50.28; H, 5.75; S, 12.21; Cl, 13.50. Found: C, 50.52; H, 5.56; S, 11.92; Cl, 13.42.

(3) Synthesis of Z-Arg(Tmo)-OH.CHA

In a mixture of 6 ml of 4N-NaOH and 25 ml of acetone was dissolved 1.85 g of Z-Arg-OH and the solution was ice-cooled. A solution (100 ml) of 2.50 g of 4-methoxy-2,3,5,6-tetramethylbenzenesulfonyl chloride in acetone was added and the mixture was stirred for 1 hour. Aqueous citric acid was added, the solvent was distilled off, and the desired product extracted with ethyl acetate and dried over anhydrous sodium sulfate. The solvent was distilled off and 0.58 ml of cyclohexylamine was added. The resulting product was crystallized from ether, filtered and dried.

Yield 2.40 g (63.1%), m.p. 127°–129° C. $[\alpha]_D^{23} +5.9°$ (c=0.84, methanol).

Elemental analysis for $C_{31}H_{47}O_7N_5S$: Calcd.: C, 58.74; H, 7.48; N, 11.05; S, 5.06. Found: C, 58.84; H, 7.30; N, 11.25; S, 5.06.

(4) Synthesis of H.Arg(Tmo)-OH

In 40 ml of ethyl acetate was suspended 2.0 g of Z-Arg(Tmo)-OH.CHA, followed by addition of 4 ml of 1N-sulfuric acid. The mixture was shaken well and washed with water and the solvent distilled off. The residue was dissolved in 40 ml of methanol and catalytic reduction was carried out in the presence of Pd black as catalyst. The catalyst was filtered off and the solvent was distilled off. To the residue was added ether and the resulting powder was collected by filtration and dried.

Yield 1.20 g (92.7%), m.p. 150°–153° C., $[\alpha]_D^{23} -4.5°$ (c=0.92, methanol).

Elemental analysis for $C_{17}H_{28}O_5N_4S \cdot \frac{1}{2}H_2O$: Calcd.: C, 49.86; H, 7.14; N, 13.68; S, 7.83. Found: C, 50.38; H, 7.57; N, 13.48; S, 7.60.

TEST EXAMPLE

Each of the $N^G$-protected arginine (approx. 20 mg) was dissolved in 2 ml of trifluoroacetic acid-thioanisole (9:1) and the solution was allowed to stand at 50° C. for 1 or 4 hours. A 100 μl portion of the solution was taken, made up to 10 ml and analyzed for arginine. The results are shown in Table 2.

TABLE 2

|  | Temperature (°C.) | Time (hrs.) | Yield of Arg (%) |
|---|---|---|---|
| H—Arg(Pme)—OH | 50 | 1 | 64 |
|  |  | 4 | 89 |
| H—Arg(Tms)—OH | 50 | 1 | 90 |
|  |  | 4 | 91 |
| H—Arg(Tmo)—OH | 50 | 1 | 30 |
|  |  | 4 | 81 |

EXAMPLE 21

(1) Synthesis of Boc-Tyr-Arg(Pme)-OH

In 20 ml of tetrahydrofuran was dissolved 790 mg of H-Arg(Pme)-OH. Then, 0.34 ml of triethylamine and Boc-Tyr-ONB (prepared from 0.57 g of Boc-Tyr-OH, 0.40 g of HONB and 0.50 g of DCC) added when cold and the mixture was stirred at room temperature for 15 hours. The solvent was distilled off and the residue was made acidic with citric acid and extracted with ethyl acetate. The ethyl acetate layer was washed with water and the solvent was distilled off. The residue was dissolved in chloroform and subjected to silica gel column (4×6 cm) chromatography. Elution was carried out with 5% MeOH/CHCl₃. The fractions containing the desired product were pooled, concentrated and precipitated from ether and the resulting powder was recovered by filtration.

Yield 690 mg (51.8%), m.p. 136°–139° C., $[\alpha]_D^{23} -15.0°$ (c=0.5, dimethylformamide).

Elemental analysis for $C_{31}H_{45}O_8N_5S \cdot H_2O$: Calcd.: C, 55.92; H, 7.12; N, 10.52; S, 4.82. Found: C, 55.95; H, 7.02; N, 10.58; S, 4.62.

(2) Synthesis of H-Tyr-Arg-OH (Kyotorphin)

In 5 ml of trifluoroacetic acid-thioanisole (9:1) was dissolved 300 mg of Boc-Tyr-Arg(Pme)-OH and the mixture was allowed to stand at 50° C. for 4 hours. The trifluoroacetic acid was distilled off under reduced pressure, ether was added to the residue and the resulting precipitate was collected by filtration. The precipitate was dissolved in a small amount of water, passed through a column (1×10 cm) of Amberlite IRA-410 (acetate-form) and lyophilized. The lyophilizate was dissolved in a small amount of water, chromatographed on a carboxymethylcellulose column (2.2×8 cm) and eluted by the linear gradient method using water (300 ml) and 0.1M ammonium acetate (300 ml). The fractions from 110 to 155 ml were pooled and lyophilized.

Yield 135 mg, $[\alpha]_D^{21} -17.8°$ (c=0.5, H₂O); amino acid analysis (acid hydrolysis): Arg 1.00(1), Tyr 0.92(1); average recovery 88.7%.

The desired compound can also be produced using Arg(Tms) or Arg(Tmo) in place of Arg(Pme). However, in the final step of removing the protective group with trifluoroacetic acid-thioanisole (9:1), it is preferable that Arg(Tms) be treated at 50° C. for 90 minutes and Arg(Tmo) at 50° C. for 5 hours.

EXAMPLE 22

(1) Synthesis of Z-Arg(Pme)-Pro-Lys(Boc)-Pro-OH

In 30 ml of methanol was dissolved 0.59 g of oily Z-Pro-Lys(Boc)-Pro-OMe prepared by serial condensation of H-Pro-OMe, Z-Lys(Boc)-ONB and Z-Pro-ONB. Catalytic reduction was then carried out in the presence of palladium black as catalyst. The catalyst was filtered off, the filtrate concentrated and the residue dissolved in 10 ml of dimethylformamide. To this solution were added Z-Arg(Pme)-OH [prepared from 0.56 g of Z-Arg(Pme)-OH.CHA], 0.15 g of HOBt and 0.23 g of DCC. The mixture was stirred at room temperature for 15 hours. The by-product DCU was filtered off and after the solvent was distilled off, the residue was dissolved in ethyl acetate and washed with aqueous sodium hydrogen carbonate and 0.2N HCl. After drying, the solvent was distilled off and the oily residue [Z-Arg(Pme)-Pro-Lys(Boc)-Pro-OMe] was dissolved in 10 ml of methanol. Then 2 ml of 1N-aqueous sodium hydroxide was added in the cold, and saponification was carried out at room temperature for 2 hours. The reaction mixture was neutralized by addition of 2 ml of 1N-hydrochloric acid when cold. After removal of the methanol by distillation, the resulting oily precipitate was extracted with ethyl acetate. The solvent was distilled off, petroleum benzin was added to the residue and the resulting powder was collected by filtration and reprecipitated from ethyl acetate-ether.

Yield 0.49 g (53.2%), m.p. 92°–96° C., $[\alpha]_D^{23} -34.4°$ (c=0.5, dimethylformamide).

Elemental analysis for $C_{44}H_{72}O_{11}N_8S$: Calcd.: C, 57.37; H, 7.88; N, 12.17; S, 3.48. Found: C, 57.09; H, 7.79; N, 11.86; S, 3.15.

(2) Synthesis of Z-Arg(Pme)-Pro-Lys(Boc)-Pro-Gln-Gln-Phe-Phe-Gly-Leu-Met-NH₂

In a mixture of trifluoroacetic acid (4.5 ml) and water (0.5 ml) was dissolved 0.49 g of Boc-Gln-Gln-Phe-Phe-Gly-Leu-Met-NH₂ and the mixture was shaken at 10° C. for 20 minutes. After addition of 0.5 ml of 1N-hydrochloric acid, the reaction mixture is distilled. Ether was added to the residue and the resulting powder was collected by filtration and dried. The powder was dissolved in 15 ml of dimethylformamide and 0.1 ml of triethylamine was added when cold. Then, 0.45 g of Z-Arg(Pme)-Pro-Lys(Boc)-Pro-OH, 0.18 g of HONB and 0.20 g of DCC were added and the mixture was stirred for 24 hours. The formed DCU was filtered off and the filtrate was concentrated. To the residue was added water and the resulting precipitate was collected by filtration and reprecipitated from ethanol-water.

Yield 0.52 g (55.2%), m.p. 245°–250° C. (decomp.), $[\alpha]_D^{23}$ −32.8° (c=0.5, dimethylformamide).

Elemental analysis for $C_{85}H_{130}O_{19}N_{18}S_2$: Calcd.: C, 57.60; H, 7.39; N, 14.23; S, 3.62. Found: C, 57.35; H, 7.48; N, 14.02; S, 3.39.

(3) Synthesis of H-Arg-Pro-Lys-Pro-Gln-Gln-Phe-Phe-Gly-Leu-Met-NH₂ (Substance P)

In 5 ml of trifluoroacetic acid-thioanisole (9:1) was dissolved 100 mg of Z-Arg(Pme)-Pro-Lys(Boc)-Pro-Gln-Gln-Phe-Phe-Gly-Leu-Met-NH₂ and the mixture was shaken at 50° C. for 4 hours. The trifluoroacetic acid was distilled off under reduced pressure, ether was added to the residue and the resulting precipitate was collected by filtration and dried. The precipitate was dissolved in a small amount of water, passed through a column (1×10 cm) of Amberlite IRA-410 (acetate-form) and lyophilized. The lyophilisate was chromatographed on a column (2.5×120 cm) of Sephadex G-25 and eluted with 30% aqueous acetic acid. The fractions rich in the contemplated compound (235–270 ml) were pooled and lyophilized.

Yield 62 mg, $[\alpha]_D^{23}$ −79.6° (c=0.5, 5% acetic acid); amino acid analysis (acid hydrolysis): Lys 1.00(1), Arg 1.03(1), Gln 2.21(2), Pro 2.15(2), Gly 0.95(1), Met 0.91(1), Leu 1.02(1), Phe 1.95(2); average recovery 85.6%.

The desired compound can also be produced using Arg(Tms) or Arg(Tmo) in place of Arg(Pme). However, in the final step of removing the protective group with trifluoroacetic acid-thioanisole (9:1), it is preferable that Arg(Tms) be treated at 50° C. for 90 minutes and Arg(Tmo) at 50° C. for 5 hours.

EXAMPLE 23

(1) Synthesis of 2,3,5-trimethylanisole

In 100 ml of DMSO were dissolved 10 g of 2,3,5-trimethylphenol and 10.4 ml of methyl iodide. Under ice-cooling, 5.6 g of 60% sodium hydride in oil was added, and the mixture was stirred at room temperature for 10 hours. After addition of water, the extraction with ether was carried out. The ether layer was washed with water and dried over anhydrous sodium sulfate. Removal of the solvent by distillation leaves the oily substance. Yield 12.9 g (quantitative)

(2) Synthesis of 4-methoxy-2,3,6-trimethylbenzensulfonyl chloride

In 500 ml of methylenchloride was dissolved 4.5 g of 2,3,5-trimethylanisole, and after cooling at −5°∼−10° C., a solution (400 ml) of 6.0 ml of chlorosulfonic acid in methylene chloride was added dropwise to the mixture. The reaction mixture was kept at room temperature and then poured into ice-5% aqueous $NaHCO_3$. The methylene chloride layer was washed with water and dried over anhydrous magnesium sulfate. The solvent was distilled off and the residue was crystallized from n-hexane and filtered.

Yield 5.0 g (67.0%), m.p. 56°–58° C.

Elemental analysis for $C_{10}H_{13}O_3SCl$: Calcd.: C, 48.29; H, 5.27; S, 12.89; Cl 14.26. Found: C, 48.42; H, 5.21; S, 12.61; Cl 14.25.

(3) Synthesis of Z-Arg(Mtr)OH.CHA

In a mixture of 10 ml of 4N-NaOH and 40 ml of acetone was dissolved 2.83 g of Z-Arg-OH and the solution was ice-cooled. A solution (10 ml) of 4.0 g of 4-methoxy-2,3,6-trimethylbenzenesulfonyl chloride in acetone was added and the mixture was stirred for three hours. Aqueous citric acid was added, the acetone was distilled off, and the desired product was extracted with ethyl acetate. Removal of the solvent by distillation leaves 4.8 g of an oily substance. This substance was dissolved in a small amount of ethyl acetate and was crystallized by addition of 1.04 ml of cyclohexylamine. The resulting crystals are recyrstallized from a mixture of methanol and ethyl acetate.

Yield 4.10 g (72.1%), m.p. 195°–197° C., $[\alpha]_D^{23}$ +6.5° (c=1.18, methanol).

Elemental Analysis for $C_{30}H_{45}O_7N_5S$: Calcd.: C, 58.14; H, 7.32; N, 11.30; S, 5.17. Found: C, 58.08; H, 7.34; N, 11.58; S, 5.32.

(4) Synthesis of H-Arg(Mtr)-OH

In 30 ml of ethyl acetate suspended 1.5 g of Z-Arg(Mtr)-OH.CHA, followed by addition of 15 ml of 0.2N-$H_2SO_4$. The mixture was shaken well and washed with water and the solvent is distilled off. The residue was dissolved in methanol and catalytic reduction was carried out in the presence of palladium black as catalyst. The catalyst was filtered off and the solvent is distilled off. To the residue was added water and the resulting crystal was obtained by the filtration.

Yield 0.77 g (81%), m.p. 100°–103° C., $[\alpha]_D^{23}$ −4.8° (c=1.30, methanol).

Elemental analysis for $C_{16}H_{26}O_5N_4S.\frac{1}{2}H_2O$: Calcd.: C, 48.59; H, 6.88; N, 14.18; S, 8.11. Found: C, 48.78; H, 7.16; N, 13.88; S, 8.29.

TEST EXAMPLE

In 2 ml of trifluoroacetic acid-thioanisole (9:1) was dissolved 20 mg of H-Arg(Mtr)-OH, and the solution is allowed to stand under the conditions as shown in Table 3. A 100 μl portion of the solution was taken, made up to 10 ml and analyzed for arginine. The results are shown in Table 3.

TABLE 3

|  | Temperature (°C.) | Time (hrs.) | Yield of Arg (%) |
|---|---|---|---|
| H—Arg(Mtr)—OH | 23 | 0.5 | 68.3 |
|  |  | 1 | 85.4 |
|  | 50 | 0.5 | 88.9 |
|  |  | 1 | 84.9 |

As is clear from data of Table 3, Mtr can be easily removed at 23° C. for one hour.

EXAMPLE 24

(1) Synthesis of Boc-Tyr-Arg(Mtr)-OH

In 20 ml of tetrahydrofuran was dissolved 0.80 g of H-Arg(Pme)-OH. Then, 0.34 ml of triethylamine and Boc-Tyr-ONB (prepared from 0.57 g of Boc-Tyr-OH, 0.40 g of HONB and 0.50 g of DCC) were added in the cold, and the mixture was stirred at room temperature for 15 hours. The solvent was distilled off and the residue was made acidic with citric acid and extracted with ethyl acetate. The ethyl acetate layer was washed with water and the solvent was distilled off. The residue was dissolved in chloroform and subjected to silica gel column (4×6 cm) chromatography. Elution was carried out with 5% MeOH/CHCl$_3$. The fractions containing the desired product were pooled, concentrated and precipitated from ether and the resulting powder was recovered by filtration.

Yield 0.6 g (51.5%), m.p. 114°–121° C., $[\alpha]_D^{23} + 1.2°$ (c=0.4, dimethylformamide).

Elemental analysis for $C_{30}H_{43}O_9N_5S$: Calcd.: C, 55.45; H, 6.67; N, 10.78; S, 4.94. Found: C, 55.12; H, 6.83; N, 10.53; S, 4.54.

(2) Synthesis of H-Tyr-Arg-OH (Kyotorphin)

In 5 ml of mixed solution of trifluoroacetic acid-thioanisole (9:1) was dissolved 400 mg of Boc-Tyr-Arg(Mtr)OH and the resulting mixture was allowed to stand at room temperature for 2 hours. The trifluoroacetic acid was distilled off under reduced pressure, ether was added to the residue and the resulting precipitate was collected by filtration. The precipitate was dissolved in a small amount of water, passed through a column (1×10 cm) of Amberlite IRA-410 (acetate-form) and lyophilized. The lyophilizate was dissolved in a small amount of water, chromatographed on a carboxymethyl-cellulose column (2.2×8 cm) and eluted by the linear gradient method using water (300 ml) and 0.1M ammonium acetate (300 ml). The fractions from 100 to 150 ml were pooled and lyophilized.

Yield 175 mg, $[\alpha]_D^{21} - 17.4°$ (c=0.5, H$_2$O); amino acid analysis (acid hydrolysis): Arg 1.00(1), Tyr 0.94(1); average recovery 86.5%.

EXAMPLE 25

(1) Synthesis of Z-Arg(Mtr)-Pro-Lys(Boc)-Pro-OH

In 30 ml of methanol was dissolved 0.59 g of oily Z-Pro-Lys(Boc)-Pro-OMe prepared by serial condensation of H-Pro-OMe, Z-Lys(Boc)-ONB and Z-Pro-ONB. Catalytic reduction was then carried out in the presence of palladium black as catalyst. The catalyst was filtered off, the filtrate concentrated and the residue dissolved in 10 ml of dimethylformamide. To this solution were added Z-Arg(Mtr)-OH [prepared from 0.56 g of Z-Arg(Mtr)-OH.CHA], 0.15 g of HOBt and 0.23 g of DCC. The mixture was stirred at room temperature for 15 hours. The by-product DCU was filtered off and after the solvent was distilled off, the residue was dissolved in ethyl acetate and washed with aqueous sodium hydrogen carbonate and 0.2N HCl. After drying, the solvent was distilled off and the oily residue [Z-Arg(Mtr)-Pro-Lys(Boc)-Pro.OMe] was dissolved in 10 ml of methanol. Then 2 ml of 1N-aqueous sodium hydroxide was added in the cold, and saponification was carried out at room temperature for 2 hours. The reaction mixture was neutralized by addition of 2 ml of 1N-hydrochloric acid when cold. After removal of the methanol by distillation, the resulting oily precipitate was extracted with ethyl acetate. The solvent was distilled off, petroleum benzin was added to the residue and the resulting powder was collected by filtration and reprecipitated from ethyl acetate-ether.

Yield 610 mg (66.1%), m.p. 90°–95° C., $[\alpha]_D^{23} - 32.7°$ (c=0.5, dimethylformamide).

Elemental analysis for $C_{43}H_{70}O_{12}N_8S$: Calcd.: C, 55.94; H, 7.64; N, 12.14; S, 3.47. Found: C, 55.62; H, 7.86; N, 11.98; S, 3.19.

(2) Synthesis of H-Arg-Pro-Lys-Pro-Gln-Gln-Phe-Phe-Gly-Leu-Met-NH$_2$ (Substance P)

In a mixture of trifluoroacetic acid (4.5 ml) and water (0.5 ml) was dissolved 0.49 g of Boc-Gln-Gln-Phe-Phe-Gly-Leu-Met-NH$_2$ and the mixture was shaken at 10° C. for 20 minutes. After addition of 0.5 ml of 1N-hydrochloric acid, the reaction mixture was distilled. Ether was added to the residue and the resulting powder was collected by filtration and dried. The powder was dissolved in 15 ml of dimethylformamide and 0.1 ml of triethylamine was added when cold. Then, 0.45 g of Z-Arg(Mtr)-Pro-Lys(Boc)-Pro-OH, 0.18 g of HONB and 0.20 g of DCC were added and the mixture was stirred for 24 hours. The formed DCU was filtered off and the filtrate was concentrated. To the residue was added water and the resulting precipitate was collected by filtration. 100 mg of the precipitate was dissolved in 1 ml of mixed solution of trifluoroacetic acid-thioanisole (9:1), and shaken at 50° C. for one hour. The trifluoroacetic acid was distilled off under reduced pressure, ether was added to the residue and the resulting precipitate was collected by filtration and dried. The precipitate was dissolved in a small amount of water, passed through a column (1×10 cm) of Amberlite IRA-410 (acetate-form) and lyophilized. The lyophilisate was chromatographed on a column (2.5×120 cm) of Sephadex G-25 and eluted with 30% aqueous acetic acid. The fractions rich in the contemplated compound (230–260 ml) were pooled and lyophilized.

Yield 58 mg, $[\alpha]_D^{23} - 78.8°$ (c=0.5, 5% acetic acid); amino acid analysis (acid hydrolysis): Lys 1.00(1), Arg 1.04(1), Gln 2.05(2), Pro 2.20(2); Gly 0.91(1), Met 0.89(1), Leu 1.05(1), Phe 1.89(2): average recovery 82.3%.

What we claim is:
1. 4-Methoxy-2,3,6-trimethylbenzenesulfonyl chloride.

* * * * *